United States Patent
Hurlstone et al.

(10) Patent No.: US 7,281,502 B2
(45) Date of Patent: Oct. 16, 2007

(54) POWERED DEVICES

(75) Inventors: Christopher John Hurlstone, Barkway (GB); Stephen Philip Kirkwood, Barkway (GB)

(73) Assignee: Team Holdings (UK) Limited, Cambridge (GB)

( * ) Notice: Subject to any disclaimer, the term of this patent is extended or adjusted under 35 U.S.C. 154(b) by 0 days.

(21) Appl. No.: 10/554,438

(22) PCT Filed: Apr. 22, 2004

(86) PCT No.: PCT/GB2004/001716

§ 371 (c)(1),
(2), (4) Date: Oct. 16, 2006

(87) PCT Pub. No.: WO2004/093948

PCT Pub. Date: Nov. 4, 2004

(65) Prior Publication Data

US 2007/0079777 A1    Apr. 12, 2007

(30) Foreign Application Priority Data

Apr. 24, 2003    (GB) .............................. 0309305.1

(51) Int. Cl.
*F02B 71/00*    (2006.01)

(52) U.S. Cl. .............................. 123/46 SC; 123/46 H
(58) Field of Classification Search ............. 123/46 R, 123/46 SC, 46 H
See application file for complete search history.

(56) References Cited

U.S. PATENT DOCUMENTS

2003/0131809 A1    7/2003    Adams

FOREIGN PATENT DOCUMENTS

| WO | WO-01/32243 A1 | 5/2001 |
|---|---|---|
| WO | WO-01/89612 A1 | 11/2001 |
| WO | WO-03/033058 A1 | 4/2003 |

*Primary Examiner*—Noah P. Kamen
(74) *Attorney, Agent, or Firm*—Barnes & Thornburg LLP

(57) ABSTRACT

Disclosed is a self-priming portable powered device such as a tool, comprising a housing within which are defined a priming combustion chamber and a main combustion chamber, within which chambers during operation of the device there is a combustion of a combustible fuel and a combustion-supporting gas; and wherein a combustion event in the priming combustion chamber causes the formation of a mixture of fuel and combustion-supporting gas in the main combustion chamber which is compressed at a pressure above ambient pressure, subsequent combustion of the compressed mixture in the main combustion chamber acting on a work piston which, directly or indirectly, performs the intended task.

13 Claims, 4 Drawing Sheets

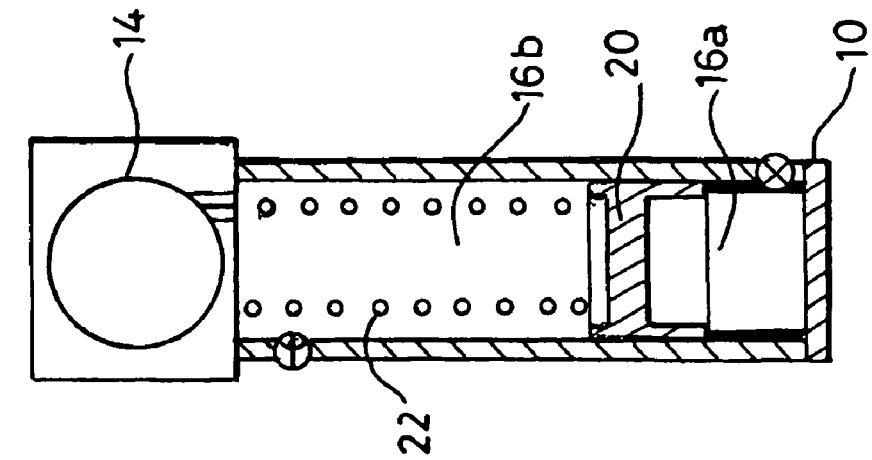
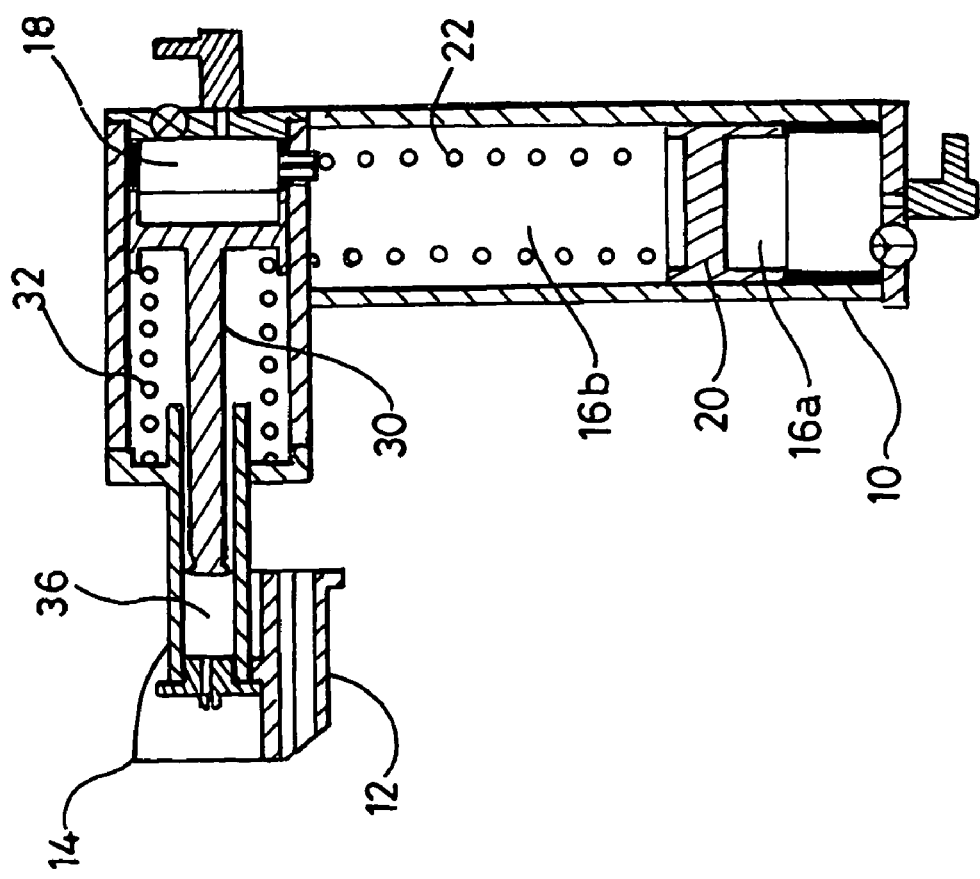
Fig. 3A
Fig. 3B

POWERED DEVICES

FIELD OF THE INVENTION

The present invention relates to a powered hand-held device, especially a device for delivering a dose of medicament to a subject.

BACKGROUND OF THE INVENTION

WO 03/033058 discloses a hand-held device powered by an internal combustion engine.

The document discloses inter alia a device, especially a device suitable for delivering a dose of medicament to a subject, wherein there is a first combustive event to perform the intended task (i.e. deliver the medicament) and a second combustive event which is used to compress a successive charge of fuel and combustion-supporting gas for a subsequent cycle of operation, such that the device is essentially self-priming. The two combustive events take place in separate combustion chambers.

The only embodiment of such a device described in detail is an arrangement whereby a priming combustion event in a priming combustion chamber causes the movement of a work piston into a primed position within a main combustion chamber, and a combustion event in the main combustion chamber causes return movement of a priming piston as well as acting on the work piston.

The present invention relates to a device which is generally similar to that disclosed in WO 03/033058 but differs therefrom in a number of respects, e.g. whilst the device of the present invention has two combustion chambers (a priming combustion chamber and a main combustion chamber), which typically communicate via one or more apertures usually incorporating associated one-way flow valve means, a combustion event in the priming combustion chamber does not cause movement of the work piston and wherein a combustion event in the main combustion chamber does not cause movement of the priming piston.

In particular, in the prior art arrangement the priming and work pistons are accommodated, and move within, a common bore (in which the respective travels of the priming and work pistons overlap) between the priming and main combustion chambers. In contrast, in the device of the present invention the priming piston and work piston are accommodated and move within separate bores and do not share a common bore.

The content of all publications cited is specifically incorporated herein by reference.

SUMMARY OF THE INVENTION

In a first aspect the invention provides a self-priming portable powered device such as a tool, comprising a housing within which are defined a priming combustion chamber and a main combustion chamber, within which chambers during operation of the device there is a combustion of a combustible fuel and a combustion-supporting gas; and wherein a combustion event in the priming combustion chamber causes the formation of a mixture of fuel and combustion-supporting gas in the main combustion chamber which is compressed at a pressure above ambient pressure, subsequent combustion of the compressed mixture in the main combustion chamber acting on a work piston which, directly or indirectly, performs the intended task.

In preferred embodiments the tool is a device for delivering a dose of medicament to a subject, by means of a hollow needle or via a needle-less injection system. The medicament may be, for example, a liquid or a dry powder.

However, the device of the invention could be used to perform many tasks or actions currently powered by other means such as motors or compressed air e.g. cutting, drilling, punching, screwing, hammering, spraying, pumping etc. However, for present purposes the invention will be described in the context of an injector device.

The priming combustion chamber and main combustion chamber are conveniently in gas-flow communication, more specifically, in substantially unidirectional gas-flow communication, such that a gas may be forced from the priming combustion chamber (e.g. in response to a combustion event therein) into the main combustion chamber, thereby pressurising a fuel/combustion-supporting gas mixture in the main chamber. The gas-flow communication between the chambers may be provided by a single aperture or a plurality of apertures, or by one or more channels, conduits, tubes, pipes or the like.

Desirably gas-flow communication between the chambers is unidirectional (from the priming chamber to the main chamber). Such unidirectional flow may conveniently be provided for by the use of unidirectional valve means. Advantageously at least one such unidirectional valve means will be associated with the or each aperture, channel, conduit, tube or pipe provided between the two chambers.

The present inventors have envisaged a number of different arrangements for the two chambers. Typically, the two chambers will be generally cylindrical. They may be arranged co-axially, end to end. They may alternatively be arranged co-axially and concentrically, such that one chamber is provided as an annulus around the other chamber. In another arrangement the two chambers may be provided in a parallel side-by-side manner. In yet another embodiment the two chambers may be provided in a perpendicular arrangement or may be joined at any other angle (not necessarily 90°).

Typically the combustion event in the priming combustion chamber acts on a priming piston or similar device located within the priming chamber, the priming piston being movable in response to the combustion event so as to force gas into the main combustion chamber. In particular the priming piston preferably does not move as a result of a combustion event in the main combustion chamber.

Conveniently there is provided a return means which acts on the priming piston so that, once the piston has reached the end of its travel within the priming combustion chamber, it is returned to its starting position ready for the next cycle of operation. A simple spring or other biasing means may be suitable for such a purpose. In order to facilitate return of the priming piston the wall of the priming chamber may be provided with one or more gas inlets incorporating one-way flow valves which allow an external gas (e.g. air at atmospheric pressure) to enter the priming chamber as the priming piston returns, thereby preventing the formation of a partial vacuum upon the return movement of the priming piston. Advantageously there are also provided one or more exhaust valves to allow exhausting of combustion products.

Whilst the device of the present invention is referred to as "self-priming" in the context of multi-cycle operation, an initial cycle of operation may, depending on the embodiment, require initial manual priming by the user—in subsequent cycles the device, however, will be self-priming.

In a preferred embodiment the device is fully automated (albeit possibly requiring an initial priming action on first use) in that one or more activations of a trigger mechanism enables the device to perform a complete cycle of operation.

If desired, the device could be arranged such that the device will continue to perform cycles of operation whilst the trigger is held, with an interlock mechanism of some kind to ensure that a single cycle of operation is performed only when the device is actually positioned in contact with a subject, and that when removed from contact the operation of the device is interrupted. Whilst at least semi-automation of the device is a desirable feature of the invention, it will be advantageous to provide a manual override to allow a user to perform a cycle of operation manually (e.g. during an initial cycle for priming, or to purge the device after use or clear blockages or mis-fires etc).

The device will advantageously comprise an interlock or other safety mechanism to reduce the likelihood of accidental discharge and prevent the device from firing unless properly primed. In particular it may be desirable to have a multi-stage actuation or triggering sequence. For example, a trigger mechanism provided on the device may have a plurality of discrete sections of travel, passage therethrough actuating various steps of the operating cycle. Alternatively, the trigger may be depressed fully (or substantially so) a plurality of times, each depression of the trigger causing actuation of different parts of the operating cycle. Yet a further arrangement is for a single actuation of the trigger being sufficient to initiate a cycle of operation, but that various parts of the cycle are subject to delay (by mechanical and/or electrical means) and that one or more sensors can interrupt or prevent parts of the cycle from occurring if conditions are not appropriate (e.g. no medicament in the medicament chamber, or the orifice of the device is not in contact with a subject). The interlock or interrupt mechanism may conveniently be operated by or dependent on input/feedback from the state of the trigger and/or a nozzle guard (e.g. depressed or released).

In a preferred embodiment there is provided a baffle member between the main combustion chamber and the priming combustion chamber and which forms a gas-tight seal with the inner surface of the housing, the baffle member comprising a one-way valve means which valve means permits entrance of the combustion-supporting gas into the main combustion chamber from the priming combustion chamber but does not permit egress of combustion products from the main chamber.

Where the device of the invention is an injection device, the device will comprise further operating features which may conveniently be generally as detailed in WO 01/89612.

The combustion-supporting gas may be oxygen or other gas comprising oxygen. Conveniently the combustion-supporting gas will be air.

The device as a whole is typically of such dimensions as to be readily hand-held in use. The barrel needs to be stable at fairly high temperatures and strong enough to withstand the high pressures generated during operation of the device, but is also desirably of low density in order to minimise the weight of the device. The barrel or housing is preferably formed from heat-resistant plastics material or metal (e.g. an aluminium alloy). The device will comprise means for forming a combustible mixture of fuel and air or other combustion-supporting gas in the main and priming combustions chamber and will generally comprise a fuel inlet and a separate air inlet. One or both of these inlets may conveniently be provided with valve means to regulate the flow of fuel or air, as the case may be.

The fuel is advantageously one which is gaseous at atmospheric pressure (760 mm Hg) and room temperature (20° C.) but which can be caused to liquefy at room temperature by mildly elevated pressure. Examples of suitable fuels include butane (which is commonly used as a fuel in disposable cigarette lighters) and propane. Desirably therefore the fuel is held as a liquid, under pressure, in a fuel reservoir. Some limited liquefaction of the fuel in the main combustion chamber may occur as a result of the high pressure immediately prior to combustion. The inventors have not found this to be a significant problem.

In preferred embodiments of the invention the device provides a substantially consistent power output from one combustive event to the next. In order to achieve this desired objective, it is advantageous to ensure that a consistent amount of fuel is present in the main combustion chamber for each combustive event. Accordingly, in preferred embodiments, the device comprises means for introducing an accurately pre-determined amount of fuel into the main combustion chamber for each combustive event.

Accordingly, in a preferred embodiment the device of the invention comprises a fuel dosing assembly for metering a dose of fuel from a reservoir of liquefied gas fuel to be delivered to the main combustion chamber, wherein the dose of liquefied gas fuel is accurately metered without undergoing a partial phase change. Specifically, in preferred embodiments, the fuel is metered through metering means whilst in the liquid phase, but allowed to vapourise upon expansion on entry into the combustion chamber (typically at atmospheric pressure at this stage of the cycle).

By way of explanation liquefied fuels such as propane and butane tend to vaporise as soon as they are removed from the elevated pressure under which they are stored. The inventors found that this phase change rendered it extremely difficult to meter an accurate dose of fuel consistently. Accordingly, in preferred embodiments it is desired that a liquefied gaseous fuel is measured and dosed whilst still under pressure (and thus in liquid form), which allows for far greater consistency of fuel dosing. Conveniently the fuel dosing assembly comprises a spool valve or a rotary valve, and suitable arrangements are disclosed in WO 01/89612. Alternatively a shuttle valve, of the type employed in pressurised metered dose inhalers, could be employed. The fuel dosing assembly valve or valves may be mechanically or electronically driven.

In preferred embodiments of the device of the invention, the fuel reservoir is pressurised, at a substantially constant pressure, which is effective in keeping all of the fuel in the reservoir in liquid form. Such active pressurising means may comprise, for example, a spring means acting on a movable pressure plate or piston within the fuel reservoir.

Similar fuel dosing arrangements may be used to introduce a dose of fuel into the priming combustion chamber.

In order to optimise the consistency of power output of the engine, it is desirable that the device will comprise priming means for introducing an accurately pre-determined amount of oxygen, air, or other combustion-supporting gas, into the main combustion chamber before each combustive event, or at least ensuring that a large proportion (over 75%, preferably over 85%, more preferably over 95%) of the combustion products are exhausted from the main combustion chamber before a successive combustive event occurs, and allowing the exhausted products to be replaced by a corresponding volume of combustion-supporting gas.

For the avoidance of doubt, it should be stated that in some embodiments, the amount of fuel and/or air (or other combustion-supporting gas) introduced into the main combustion chamber can be altered between predetermined, fixed amounts. Thus, the power output of the device is consistent for a given volume of fuel and air, but these can be adjusted as desired, to increase or decrease the power output of the device between pre-determined set values. Thus, for example, the fuel dosing assembly may be arranged to meter one of several, fixed amounts of fuel. Preferably the fuel and/or air inlets, by which the fuel and air (or other combustion-supporting gas) are respectively introduced into the main combustion chamber, will be shaped so as to set up turbulent flow, facilitating mixing of the fuel and air upon entry into the main combustion chamber. Forcing fuel and/or air through one-way valve means provided in a baffle plate member is one convenient method of establishing turbulent flow and/or causing thorough mixing. Also, introducing air or other gas into the combustion chamber tangentially, rather than radially, is another method of improving mixing of the fuel/gas mixture.

It will be apparent that in a device in accordance with the invention defined above, in which the main combustion chamber is pressurised prior to ignition of the air/fuel mixture, such superatmospheric pressure would tend to displace the work piston or pistons communicating with the main and priming combustion chambers. In order to resist this the device preferably comprises a restraining means, acting directly or indirectly on the piston/pistons, which serves to keep the piston/s in place against the pressure of the compressed air/fuel mixture, but which is insufficient to restrain the piston when the air/fuel mixture is ignited. In one embodiment the device is provided with one or more spring-biased fingers, typically mounted or acting generally perpendicular to the direction of travel of the piston, which fingers engage co-operatively shaped recesses on the pistons or associated shaft, the spring-biasing acting to urge the fingers into engagement with and thereby restrain, the piston or associated shaft. In an alternative embodiment the restraining member takes the form of a resiliently-deformable, or a rupturable, retaining device. An example of a rupturable retaining device is a shear pin, or similar, which can secure the piston (or work member). In another embodiment the restraining means comprises one or more struts spring-biased, resiliently deformable or deflectable, so as to be displaceable, mounted generally parallel to the direction of travel of the piston, but with an angled surface at the upper end proximal to the piston, the strut or struts being displaceable outwards by the piston upon combustion. Preferably the restraining means automatically re-sets after each cycle of operation—accordingly a shear pin is a less preferred arrangement than a resiliently deformable or deflectable member.

The ignition means conveniently takes the form of a spark plug. This may be powered by a piezoelectric ignition circuit e.g. of the type disclosed in EP 0316468. In preferred embodiments the ignition means will be interlocked such that it is inoperable unless the rest of the device is in a primed state ready to fire. A further preferred feature is that the ignition means can be disabled as soon as combustion has commenced, in order to conserve electrical energy. It may also be desired to limit the electrical output of the ignition means to below the breakdown voltage of the spark gap, and then initiate spark formation in a controlled manner. Controlled ignition may be achieved, for example, by means of a pulse transformer (as used in electronic flash apparatus) or by means of a piezoelectric spark generator, itself insufficient to cause ignition but capable of opening an ionization path for the main spark to follow. Typically the ignition circuit will comprise one or more capacitors and a voltage transducer coil. It is preferred that the spark voltage/power is maintained at a substantially constant value, as this has an effect on the consistency of the combustion in the main combustion chamber.

A device in accordance with the invention will generally comprise one or more further components associated with a conventional internal combustion engine. In particular, the device will conveniently comprise at least one exhaust outlet to allow the products of combustion to exit the main and priming combustion chambers.

The device may be used to deliver a medicament to a human subject or to any animal subject, including birds (especially poultry), farm livestock (such as sheep, pigs, cattle, goats, horses), and companion animals (especially cats and dogs). It is desirable to minimise the noise of operation of the injection device to avoid discomfort or irritation to the recipient of the medicament, and any nearby people or animals. The inventors have noted that, in this respect, it is desirable that the residual energy of the products of the main combustion is at least largely dissipated before the exhaust valve is opened, so that venting of the cylinder following combustion is accomplished quietly.

Exhausting of the priming and main combustion chambers may take place substantially simultaneously e.g. in response to a single signal or trigger (e.g. electrical and/or mechanical), which causes the substantially simultaneous opening of appropriately positioned exhaust valves in the priming and main chambers.

For instance, the priming combustion event may act on the priming piston which is then held in a displaced position (compressing the fuel/gas mixture in the main chamber) by the pressure exerted by the expanded combustion products in the priming chamber behind the piston—in such an embodiment, there may be no absolute requirement for a one way valve or other unidirectional flow means between the priming chamber and the main chamber, although a unidirectional flow means of some sort is still preferred.

Alternatively, the priming and main combustion chambers may be exhausted at different times during the operating cycle of the device.

As an example of a preferred embodiment of this sort the priming piston, after having forced gas into the main chamber, may be allowed to return to its pre-combustion "home" position, the superatmospheric pressure being maintained in the main chamber by a unidirectional flow means such as a one-way check valve or similar (and by retaining means acting to prevent displacement of the work piston). In this embodiment, it can be arranged that displacement of the work piston (in response to a combustive event in the main chamber) can cause venting of the combustion products from the priming chamber. To facilitate this, there may be provided gas flow communication between the main chamber and the priming chamber, conveniently unidirectional gas flow communication (from the main chamber to the priming chamber i.e. in the reverse direction to that which allows for compression of the fuel/gas mixture in the main chamber). More specifically, a conduit, aperture, tube, pipe or the like may be provided in the main chamber such that air or other gas displaced by the work stroke or downstroke of the work piston may be forced into the priming chamber, in turn displacing the combustion products therefrom through an exhaust valve timed to open at an appropriate juncture. Such a feature of operation preferably takes place when the priming piston is at or near its "home" position, since this reduces the volume of gas to be displaced from the priming chamber.

The device will also further advantageously comprise return means, to return the work piston to a primed position when the device has been fired. The return means may comprise a simple spring biasing means, such as a compression spring which is compressed by the stroke of the piston such that, when the force on the piston from the compressed spring is greater than the force exerted by the gaseous post-combustion products, the piston will tend to return to its primed position (once the exhaust valve or valves have opened). Alternatively, or additionally, the depression of the piston can be used to compress gas in a compartment beneath the piston, thus leading to an increase in pressure acting upwards on the piston which, when it becomes greater than the downward pressure of the combustion products acting on the piston, will tend to return the piston to its primed position. An arrangement incorporating both of these features is disclosed in EP 0 316 468. Similar return means may conveniently be provided to act on the priming piston.

Conveniently a work member may be associated with the work piston and typically takes the form of a metallic (e.g. steel) piston rod or push rod welded, screw-threaded or otherwise operably linked with the work piston. It should be noted that it is not essential for the work member to be rigidly attached, or physically connected, to the piston. For example, the operable linkage between the piston and the work-member could take the form of a hydraulic fluid-filled conduit, the hydraulic fluid in the conduit serving to transfer energy from the piston to the work member. Additionally or alternatively, one or more solid intermediate members may be disposed between the piston rod and the work member. Such an intermediate solid member may be generally referred to as a "striker". In such an arrangement the piston or piston rod never comes into physical contact with the work member. A preferred arrangement provides a temporary separation (e.g. a small, air-filled gap) between the piston rod and the work member and/or any intermediate striker—the piston initially being separated from the work member or intermediate member when the device is primed, which separation allows the piston to reach a higher velocity (following combustion) before contacting the work member and/or intermediate member. Accordingly, greater initial acceleration is conferred on the work member than would have occurred if the piston was in physical contact (or otherwise rigidly-linked) with the work member at all times.

It is particularly envisaged that the device of the invention may be used as a means to administer a medicament to animals or to use in mass vaccination/inoculations of human subjects (e.g. in schools, universities, work places or other large institutions).

It will normally be preferred that the device of the invention will perform only a single combustive event when the trigger is actuated so as to avoid, for instance, inadvertent repeated injection of a subject. It will, however, be preferred that the device is provided with sufficient reserves of fuel and (if appropriate) electrical energy that it will be capable of performing a plurality (e.g. a minimum of 1000 or 2000) firing cycles before the fuel and/or electrical energy reserves (if present) are exhausted.

The medicament chamber of the device may contain sufficient medicament for just a single dose for delivery to the subject, so as to require replenishment with medicament after delivery of each dose of medicament. Alternatively, the medicament chamber may contain sufficient medicament for a plurality of doses, such that only occasional replenishment is required. In the latter situation, the medicament chamber will conveniently be provided or associated with dosing means, such that an appropriately-sized, measured dose of medicament is delivered each time the device is used. Desirably the dosing means is adjustable between different positions so that various pre-determined doses of medicament may be delivered.

The medicament chamber may form an integral part of the device of the invention, or may take the form of a readily removable component.

Needleless injectors per se are well known to those skilled in the art. Examples of such devices include those disclosed by Schwebel et al, which are powered by a pyrotechnic charge (see U.S. Pat. Nos. 3,802,430; 4,089,334 and 4,124,024).

It is desirable that devices such as needleless injectors have a consistent power output: whilst, on one hand, sufficient power must be provided to force the medicament or other substance through the skin, it is necessary to avoid the use of too much power, otherwise the substance may be injected deeper than is required and may cause greater disruption to the tissues (especially blood vessels) of the subject than is required, leading to extensive and unsightly bruising, and cause pain.

Those skilled in the art will be acquainted with the types and doses of substances which are deliverable by a needleless injector. A typical dose volume will be between 0.01 ml and 2.0 ml. The substance to be delivered may take the form of a liquid (a solution or suspension), but other formulations may be employed.

Ideally, in order to reduce or minimise sensation of pain associated with the injection, the medicament should be administered within an injection interval of less than 500 milliseconds, preferably about 200 milliseconds. Further, in an ideal embodiment, there is an initial peak in the injection pressure provided by the injector in order to overcome the resistance created by the subject's skin, followed by a longer, sustained pressure of lower magnitude to deliver the medicament dose. The initial penetrating pressure should not be so high as to cause excessive damage to the skin or tissue, and is typically in the range 100 to 800 bar, depending on the subject. The subsequent pressure must not drop so low as to result in incomplete injection of the medicament, and is advantageously in the range 50 to 400 bar, depending on the subject.

An injection device orifice, through which the medicament is expelled, will conveniently have a diameter in the range 0.1-0.5 mm, more preferably in the range 0.12-0.45 mm. An orifice of these dimensions, with average forces of the magnitude described above, would create an initial medicament velocity of about 120 m/s to penetrate the skin, with the rest of the medicament dose being delivered at a velocity of about 70 m/s. A preferred velocity is in the range 50-150 mls, which is found suitable for transdermal delivery of most or all of an average dose of medicament to a typical human subject.

The invention will now be described by way of illustrative example and with reference to the accompanying drawings, in which:

FIGS. 3A and 3B are schematic sectional views of a further embodiment of a device in accordance with the invention;

EXAMPLE 1

Figure 1:
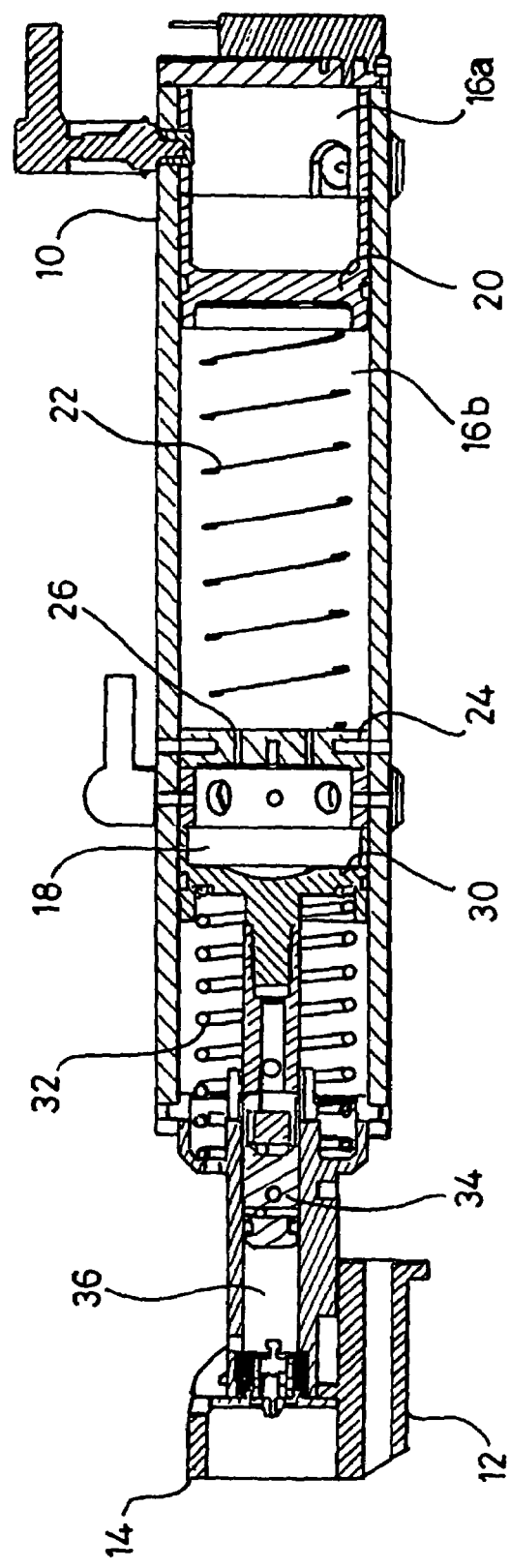
FIGS. 1 and 2 are longitudinal sectional views of one embodiment of a device in accordance with the invention, suitable for delivering a dose of a medicament to a subject.
Figure 2:
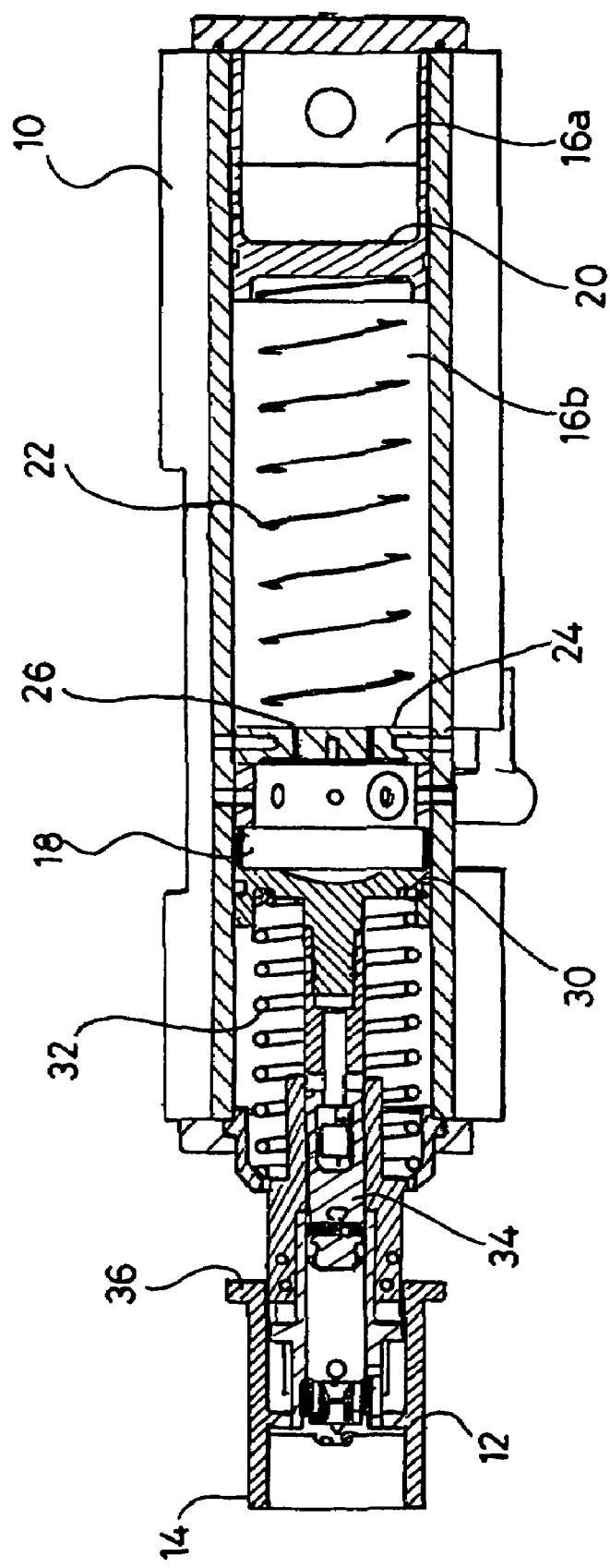

This example relates to a self-priming injection device in accordance with the invention. The device is shown in longitudinal sectional view in FIG. 1 and in FIG. 2, the plane of the section in FIG. 2 being at 90° to the section in FIG. 1. Referring to FIGS. 1 and 2, the device comprises a generally cylindrical housing or barrel 10 formed from aluminium. The layout, dimensions and materials are typical of medicament using jet pressures in excess of 300 bar. The inner bore of the barrel 10 is about 36 mm in diameter. The overall length of the complete device is about 30 cm. Towards one end of the barrel 10 is a nozzle assembly indicated generally by reference numeral 12 and comprising a displaceable nozzle guard 14. Within the barrel 10 is a priming combustion chamber 16 disposed towards one end and, disposed towards the opposed end region of the barrel 10 is a main combustion chamber 18. Both the priming combustion chamber 16 and the main combustion chamber 18 are generally cylindrical.

Within the priming chamber 16 is located priming piston 20, which forms a fluid-tight seal with the inner wall of the chamber, by means of a silicon rubber O ring seal, seated within a groove on the piston 20. The seal effectively partitions the priming combustion chamber 16 into an "upper" part 16a (within which the actual combustion event takes place) and a "lower" part 16b.

The upper part of the chamber 16a comprises a fuel inlet and an air inlet to allow for the formation in the upper part 16a of a combustible mix of butane (or other fuel) and air (or other combustion-supporting gas).

The priming piston 20 is able to move bi-directionally within the priming chamber 20. Thus, for example, in response to a combustive event occurring in the upper part 16a of the chamber, the piston is displaced towards the main combustion chamber 18. Equally, a return means, comprising compression spring 22 (shown schematically in the Figures), is able to return the piston 20 to its starting position. The spring 22 is positioned between a fixed baffle plate 24 and the underside of the priming piston 20, which includes a recessed portion (or alternatively, an annulus) to accommodate one end of the spring.

The lower part 16b of the priming chamber is in unidirectional gas flow communication with the main combustion chamber 18. Gas flow communication is afforded by apertures 26 (about 2 mm in diameter) in the baffle plate 24. Each aperture 26 is equipped with a one-way check valve, such that gas may pass from the priming chamber 16b into the main combustion chamber 18, but gas (such as combustion products) cannot pass in the reverse direction from the chamber 18 into the lower part 16b of the priming chamber. The baffle plate 24 is covered (on the main chamber side) by a thin valve plate of stainless steel. A positive pressure differential between the lower part 16b of the priming chamber and the main chamber 18 deflects the valve plate away from the baffle plate 24 allowing gas to enter the main chamber, whilst a negative pressure differential forces the valve plate against the baffle plate 24, closing the apertures.

Located within to the main combustion chamber 18 is a work piston 30. The work piston 30 is retained in its initial position, against the superatmospheric pressure of a compressed fuel/gas mixture in the main combustion chamber 18, by a work piston return means, comprising compression spring 32 which is seated at one end within a groove provided on the underside of the piston 30 and, at the other end, abuts against the end surface of the barrel 10.

The work piston 30 is displaceable, against the spring 32, in response to a combustion event in the main chamber 18. The displaced piston 30 eventually impacts, and causes movement of, a striker/plunger assembly 34, which in turn causes ejection of a dose of medicament from the nozzle of the device.

In addition to the aforementioned components, the device further comprises an ignition source, trigger mechanism, exhaust system, fluid-tight seals between various components and various valves, vents and ports, all of conventional design. The operation of the vents etc. may be mechanical or electrical (e.g. solenoid operated).

The general operation of the device will now be described.

Starting from an unprimed system (as illustrated in FIGS. 1 and 2), the first action is for fuel to be metered into each of the two combustion chambers 16, 18. All exhaust ports are closed at this point and the work piston 30 is in its "home" position. Following the fuel metering, either as a timed event or on some additional external trigger, the essentially uncompressed fuel/air mix in the priming combustion chamber 16 is ignited, causing combustion to occur. The resulting rapid pressure rise causes the priming piston 20 to move forward, forcing the air in front of it into the main combustion chamber 18 through the one way valves associated with the baffle plate 24. The work piston 30 is held in place against the rise in pressure by a release mechanism of some kind e.g. deflecting struts.

After a short period of time a second spark occurs, this time in the main combustion chamber 18, causing the pressurised fuel/air mix therein to ignite. The resulting pressure rise drives forward the work piston past the release mechanism and hence, for a medicament delivery device, directly or indirectly drives forward the plunger 34 and ejects the dose from dose chamber 36.

At the appropriate points in this cycle, exhaust ports in both combustion chambers 16, 18 open to allow return of the corresponding pistons 20, 30, aided by some form of returning assembly or element (e.g. springs), thus exhausting of the bulk of the combustion products. Air inlets into the various chambers, checked to give one-way flow only as required, assist the return of the two pistons and prepare the system for the repeat sequence.

In greater detail, the illustrated embodiment operates as follows:

The priming piston 20 is in contact with the priming combustion chamber 16, held in place by the priming piston return means, in this case spring 22. All exhaust ports are closed.

Upon activation of a trigger of some kind, fuel is dispensed into both combustion chambers via inlet ports. Fuel is typically butane but may also be propane or any other appropriate fuel, or indeed a mixture of fuels. It is metered in the required volume in the liquid phase and dispensed into the chambers. Fuel may be metered from a single reservoir into a feed manifold which then feeds the two chambers in the required proportion, or via two separate dispensing valves, one for each chamber. The trigger input for fuelling to take place can either be a mechanical input from the user, such as the pulling of a trigger lever or pushing of a button, or by the motion of other features on the device such as a displaceable nozzle guard 14.

The fuelling system is arranged such that it is not possible to carry out repeat dosing of fuel prior to activating the device. In other embodiments, fuelling of one or both chambers may have taken place as part of the final section of the overall sequence.

Fuelling of both chambers is followed, either automatically or via a further trigger input, by the ignition of the (uncompressed) fuel/air mix in the priming chamber 16.

Ignition can be caused in a number of ways—the illustration shows a typical small spark plug but customised alternatives can be used instead. The location of the spark plug is also flexible, as is the number used for each chamber.

Given a spark of sufficient power and voltage generated by an incorporated ignition circuit, and an appropriate fuel/air mix, ignition of the gases occurs leading to rapid pressure and temperature rise in the priming chamber 16. This rapidly rising pressure generated by the combustion drives forward the priming piston which pushes the air in front of it through the baffle plate 24 and into the main combustion chamber 18. An air inlet check valve located close to the baffle plate for the purposes of allowing air back into the priming chamber is such as to prevent any reverse flow of air out of the priming chamber during this motion.

The size of the priming combustion chamber 16, the amount of fuel used, and the strength of the return element are such as to ensure that the energy available from the combustion process is sufficient to give full travel of the priming piston 20 and the full priming of the main combustion chamber with air. The front of the priming piston 20 has a recessed portion into which the return spring 22 is compressed.

The baffle plate 24 to the rear, and the work piston 30 in front, close off the main combustion chamber 18 which now contains a pressurised mixture of fuel and air. The actual pressure can be controlled through selection of the appropriate travel geometries and combustion chamber volume, and is typically of the order of 2-6 bar for the configuration described. The work piston is secured in position against this pressure by springs and/or releasable mechanical elements (e.g. in the form of two deflecting metal release struts which deflect to release the piston once a given load threshold is reached and return to the engaged position as the piston returns). The plunger 34 is in a retracted position towards the rear of the dose chamber 36 which contains the dose to be delivered.

At the appropriate moment, a trigger is activated which results in ignition of the compressed fuel air mix, leading to combustion in the main combustion chamber 18. When the combustion pressure rises above a specific level, the work piston 30 is released by the releasable mechanical elements and moves forward, transferring its forward motion to the plunger 34 via one or more fixed or movable links. Hence the plunger 34 moves forward through the dose chamber 36, expelling the dose as a result.

The air in front of the work piston 30 is emitted through vents in the barrel 10, preventing any build up of pressure which could resist the forward motion of the work piston 30. This stage of the sequence is complete when the work piston 30 and plunger 34 have travelled fully forward, and the priming piston 20 has travelled to its full extent backwards within the barrel 10.

The next part of the sequence begins when the exhaust port in the main combustion chamber 18 is opened at which point the work piston 30 and plunger 34 are driven back towards the front of the main combustion chamber, by return spring 32. The effect of this motion is to exhaust the combustion gases from the system and return these components to their starting positions, with the mechanical release elements re-setting themselves to a position which retains the work piston. Because the area directly in front of the work piston is open to atmosphere, air can enter this area freely as the piston moves back. Any compressed air in the spring recess in the front of the priming piston will also vent through the baffle plate at this stage.

Because of the pressures and contact forces involved and the desire to keep the exhaust mechanism as small as practicable, it may be necessary for any mechanical exhaust system to give some mechanical advantage such that the actuation force, however applied, is not too high. This can be achieved in a number of ways, such as through the inclusion of linkages and/or levers.

One solution would be to link the state of one or both exhaust ports to the position of the sprung nozzle guard 14 which is maintained in the extended position until just before filing when the action of the operator displaces the guard into a retracted position by applying a force against target surface. When the nozzle guard 14 is depressed, the exhaust valve could be closed (prior to fuel being introduced) and combustion can take place, but when the guard is released (just after firing) the exhaust port returns to its normally open state, allowing expulsion of combustion products from the chamber or chambers by the returning corresponding pistons.

In the illustrated embodiment, exhausting of the priming combustion chamber 16 takes place at the same time as the exhausting of the main combustion chamber 18, with the exhaust valve in the chamber activated at the same time and possibly by the same signal/mechanism. A check valve located in the priming chamber close to the baffle plate 24 allows air to enter into the area behind the priming piston as it returns to its home position.

The full volume of the priming combustion chamber is not evacuated during exhausting, so the supporting gas for the subsequent combustion event in this chamber would nominally be largely composed of the combustion product from the previous operation. Leaving the exhaust port open for as long as possible and maximising the aperture of the exhaust port(s) will prevent this by allowing enough clean air into the chamber to support the combustion process.

The work piston 30 and other "dose delivery" components need to be self-positioning as part of the re-priming process. For a single work piston/plunger component this is not an issue as the return of the work piston automatically re-positions the plunger to which it is fixed. For configurations incorporating separate work piston, plunger and striker components, self-priming is more complex.

In the illustrated embodiment this is achieved by having the plunger 34 connected to the work piston 30 via a rigid linkage which runs freely through the centre of the work piston and the striker component. When, during combustion, the work piston accelerates forward, it passes freely over the link and hence the plunger (and striker) do not move. It is only when the front face of the work piston strikes the back face of the striker that these components begin to move forward, separately at first but then coalescing together to form a single unit which drives the dose out of the chamber. On its return, the work piston does not pick up the linkage immediately and hence the gap between piston and striker is re-established. The striker is pulled into position in between the piston 30 and plunger 34 by an externally applied force e.g. from magnets housed in the dose chamber.

Depending on the overall configuration of the device, re-filling of the dose chamber may also need to take place automatically. When the work piston 30 pulls the plunger 34 back, a check valve in the nozzle prevents air being drawn in through the orifice. The resulting suction instead draws a new dose through a feed line from a dose reservoir (either a bottle, held within the device, or a hose line to separate tank). A check valve in this feed line close to the chamber inlet prevents back flow of dose during actuation.

EXAMPLE 2

A further embodiment of a device in accordance with the invention is shown schematically in FIGS. 3A and 3B. The plane of the section shown in FIG. 3B is at 90° to the plane of the section in FIG. 3A.

The embodiment shown in FIGS. 3A, B is essentially similar to that depicted in FIGS. 1 and 2, and like components are denoted by common reference numerals. The main difference between the two embodiments is that in the example shown in FIGS. 3A, B, the priming chamber 16 is rotated through 90° such that its long axis is perpendicular to the long axis of the main combustion chamber 18.

As well as offering a more compact overall shape, there are other potential benefits, including:

the spark plug (or other ignition means) for the main combustion chamber 18 may be mounted on the end face and thus adopt a more central location within the combustion chamber 18, which in turn should give greater consistency of ignition and combustion profile;

the air inlet from the priming chamber into the main chamber can adopt a more tangential and less radial position, which should improve mixing of the fuel/air mixture in the main chamber prior to ignition;

it is easier to manufacture the device with the main and priming chambers having a different diameter bore than for the arrangement described in Example 1.

Unidirectional gas flow communication between the priming chamber 16 and the main chamber 18 is provided by a short aperture 26 within which is located a one-way check valve.

Appropriate venting etc. is achieved by suitably timed operation of exhaust valves 40, 42 in the priming and main combustion chambers respectively. Air enters the priming chamber 16 via one-way check valve 44 as the priming piston 20 returns to its starting position.

EXAMPLE 3

Figure 4:
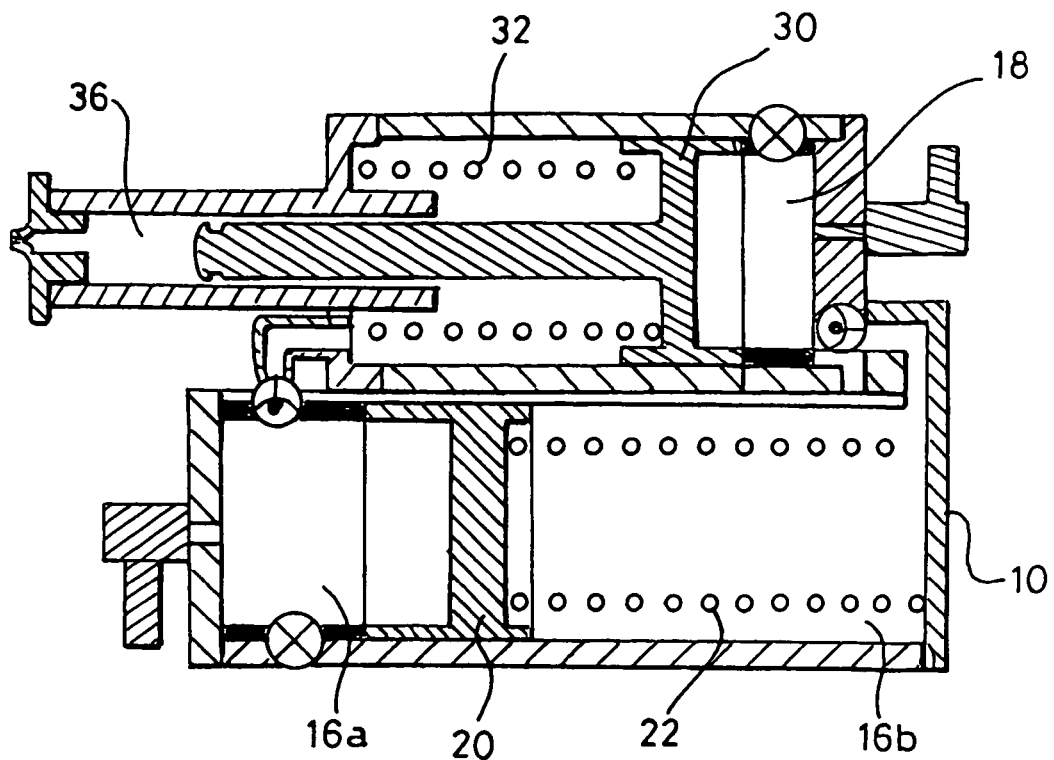
FIG. 4 is a schematic sectional view of another embodiment of a device in accordance with the invention.

This relates to another embodiment of a device in accordance with the invention, which is illustrated in a schematic sectional view in FIG. 4. Again, the illustrated embodiment is similar in terms of essential components and general operation to that described in Examples 1 and 2. In this example, the priming chamber 16 is rotated through a further 90° (relative to Example 2) such that the long axes of the priming and main combustion chambers are parallel but offset, the priming chamber being mounted beneath the main chamber and oriented in the opposite direction. Again, like components are denoted by common reference numerals.

The sequence of operation is essentially as described in Examples 1 and 2, with the motion of the priming piston 20 forcing air into the main combustion chamber 18 through conduit 26 which incorporates a one-way check valve to give the required pressurised fuel/air mix.

A variation on the next part of this sequence is for the combustion in the main combustion chamber to be delayed and for the exhaust valve 40 on the priming combustion chamber to be opened. As illustrated in FIG. 4, this could be effected either by a mechanical input, including a pilot pressure pulse signal taken from, say, the combustion chamber, or by a timed electrical signal. With this exhaust valve opened the priming piston 20 is driven back to its home position by the return spring, at which point ignition in the main chamber 18 now takes place. The benefit of this delay is that air pushed in front of the work piston 30, which is normally exhausted from the device, can now be ported through the priming combustion chamber 16 (on which an exhaust valve also opens) via a one way check valve 50, driving out a large proportion of the combustion products and leaving a majority of clean air in the priming chamber for the subsequent operation.

This approach can easily be incorporated into the embodiments described in Examples 1 and 2 through the use of, for example, connecting tubing to give a flow path for the air from the front of the work piston up to and into the priming chamber, the sequence of exhausting and piston movement being modified as described above.

The alternative configuration shown also gives additional scope for mechanical operation of the exhaust valves due to the close proximity of the valves to the nozzle and the nozzle guard (not shown in FIG. 4), the motion of which may more readily be linked to valve operation if required.

EXAMPLE 5

Figure 5:
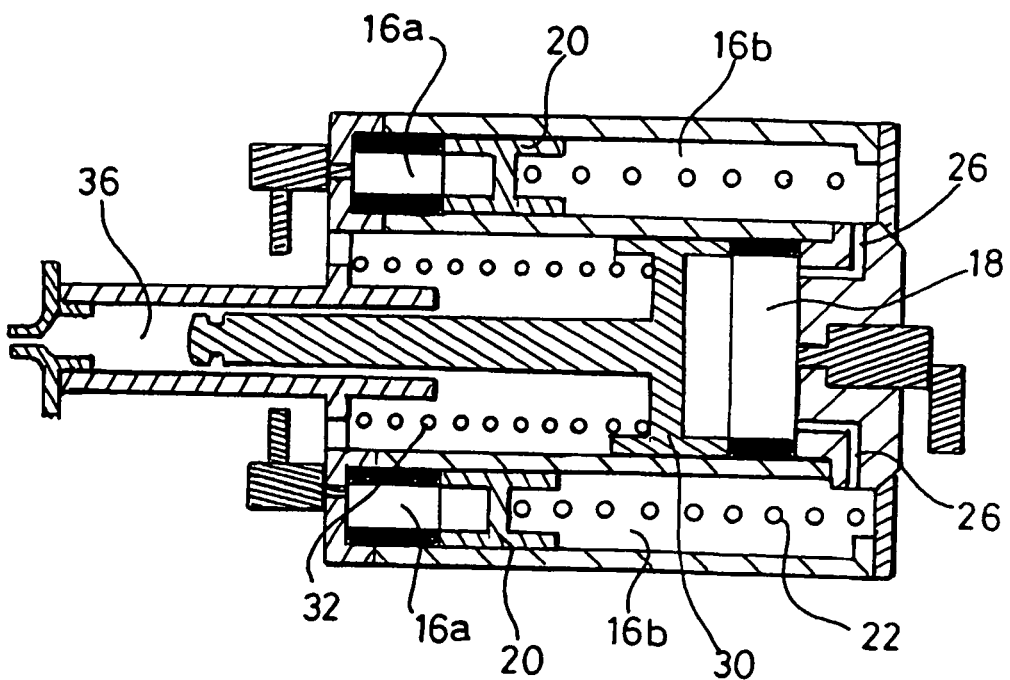
FIG. 5 is a schematic sectional view of yet another embodiment of a device in accordance with the invention.

This relates to yet another embodiment of a device in accordance with the invention. Again, the essential components and general principle of operation are as described in the preceding examples. A schematic sectional view of the further embodiment is shown in FIG. 5. Again, like components are denoted by common reference numerals.

In this embodiment the priming combustion chamber 16 is generally annular and substantially surrounds the main combustion chamber 18. Air from the priming chamber 16 is forced into the main chamber 18 through conduits, associated with one-way check valves, to provide a pressurised fuel/air mix in the main chamber. The valving and exhausting options may be as those described in the preceding examples.

The invention claimed is:

1. A self-priming portable powered device or tool, comprising a housing within which are defined a priming combustion chamber and a main combustion chamber, within which chambers during operation of the device there is a combustion of a combustible fuel and a combustion-supporting gas; and wherein expansion of oases as a result of a combustion event in the priming combustion chamber forces a combustion-supporting gas into the main combustion chamber so as to cause the formation therein of a mixture of fuel and combustion-supporting gas which is compressed at a pressure above ambient pressure, subsequent combustion of the compressed mixture in the main combustion chamber causing expansion of gases therein to act on a work piston which performs the intended task.

2. A device according to claim 1, wherein a combustion event in the priming combustion chamber displaces a priming piston from a home position to a displaced position, and wherein movement of the priming piston from the home position to the displaced position forces a combustion-supporting gas into the main combustion chamber, so as to cause formation of a compressed mixture of fuel and combustion-supporting gas in the main combustion chamber.

3. A device according to claim 2, wherein the priming piston and work piston are accommodated and move within separate respective bores.

4. A device according to claim 3, wherein the separate respective bores are parallel.

5. A device according to claim 3, wherein one of the bores is in the form of an annulus substantially surrounding the other bore.

6. A device according to claim 3, wherein the bores are co-axial and arranged end-to-end.

7. A device according to claim 3, wherein the bores are at an angle to one another of between 1 and 180°.

8. A device according to claim 1 wherein the combustion-supporting gas comprises air.

9. A device according to claim 1 wherein a unidirectional gas flow communication means is provided so as to allow for unidirectional gas flow from the priming chamber to the main combustion chamber.

10. A device according to claim 9, wherein the unidirectional gas flow communication means comprises one or more one-way valves.

11. A device according to claim 1, wherein there is provided a gas flow communication means to allow a gas, displaced from the main combustion chamber by movement of the work piston, to exhaust combustion products from the priming combustion chamber.

12. A device according to claim 11, wherein the gas flow communication means allows unidirectional gas flow.

13. A device according to claim 11, wherein exhaustion of the combustion products from the priming combustion chamber takes place when the priming piston is at or near its "home" position.

* * * * *

UNITED STATES PATENT AND TRADEMARK OFFICE
Certificate

Patent No. 7,281,502 B2  Patented: October 16, 2007

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Christopher John Hurlstone, Barkway (GB); Stephen Philip Kirkwood, Barkway (GB); and Andrew Robert Fry, Barkway (GB).

Signed and Sealed this Ninth Day of July 2013.

*STEPHEN K. CRONIN*
*Supervisory Patent Examiner*
*Art Unit 3747*
*Technology Center 3700*